United States Patent [19]

Barnes

[11] Patent Number: 4,569,339

[45] Date of Patent: Feb. 11, 1986

[54] CHIROPRACTIC TABLE LOCKING DEVICE

[76] Inventor: James E. Barnes, 1814 Clover Land Dr., Fort Wayne, Ind. 46804

[21] Appl. No.: 535,607

[22] Filed: Sep. 23, 1983

[51] Int. Cl.$^4$ .......... A61F 5/00

[52] U.S. Cl. .......... 128/74; 128/73

[58] Field of Search .......... 128/73, 74

[56] References Cited

U.S. PATENT DOCUMENTS

| | | | |
|---|---|---|---|
| 1,337,145 | 4/1920 | McManis | 128/74 |
| 1,351,482 | 8/1920 | McManis | 128/74 |
| 1,371,502 | 3/1921 | McManis | 128/74 |
| 1,400,546 | 12/1921 | Holme | 128/74 |
| 1,417,675 | 5/1922 | McManis | 128/74 |
| 1,453,013 | 4/1923 | Koenigkramer | 128/74 |
| 1,626,091 | 4/1927 | Macklin | 128/74 |
| 1,626,471 | 4/1927 | Miller | 128/73 |
| 4,144,880 | 3/1979 | Daniels | 128/74 |
| 4,489,714 | 12/1984 | Barnes | 128/74 |

*Primary Examiner*—Paul J. Hirsch

*Attorney, Agent, or Firm*—George A. Gust

[57] ABSTRACT

Disclosed is a chiropractic table having an elongated, body-supporting table mounted upon a base and being centrally divided into upper and lower body supporting portions, the lower body-supporting portion being pivotally mounted at the end thereof proximal said upper body supporting portion for side-bending, rotation, and deflection movement about vertical, longitudinal, and horizontal axes, respectively. Locking mechanisms are provided for selectively locking the lower body-supporting portion in selected side bending and rotation positions.

2 Claims, 6 Drawing Figures

CHIROPRACTIC TABLE LOCKING DEVICE

BACKGROUND OF THE INVENTION

1. Field of the Invention

The present invention relates to chiropractic tables for supporting and manipulating a patient during chiropractic treatment and in particular to such a table which can be locked in selected side-bending and/or rotation positions.

2. Description of the Prior Art

Many procedures used by chiropractors in treating their patients utilize a specialized, articulated table for supporting the patient during the procedure. Such tables, well known in the prior art, typically include an upper and a lower body-supporting portion, the two portions defining a patient supporting table. The table is typically padded, adjustable, and articulated so that a patient, lying freely on the table, or strapped thereto, can have the musculo-skeletal system manipulated as required for a particular procedure. Manipulation of the table itself is performed by the chiropractor, frequently, simultaneously with the application of massage or other manual manipulation.

Typical of such prior art tables are those manufactured by Custom Tool, Inc, assignee of the present invention, one such table being disclosed in co-pending U.S. patent application Ser. No. 456,511 by James E. Barnes, filed Jan. 7, 1983. In such prior art tables, however, it has been common practice to provide a lower body-supporting portion which can be pivoted or rotated about a longitudinal axes and pivoted about a vertical axis adjacent the patient's waist to effect rotation and side-bending movement. This rotation and side-bending movement can be performed when the lower body-supporting portion is unlatched. Under such conditions, the lower body-supporting portion is freely movable and all movement thereof is controlled entirely by the chiropractor. It is necessary for the practitioner to use one or both hands, or otherwise manually to move and then hold the table in a predetermined position.

There is a need to have such a chiropractic treatment table which can be moved into a selected rotation or side-bending position and then locked in such position so that the practitioner's hands are totally free to perform other manipulations required by a particular procedure.

SUMMARY OF THE INVENTION

In its broader aspects, there is disclosed a chiropractic treatment table which comprises a base and an elongated, body-supporting table mounted thereon, the table being centrally divided into upper and lower body-supporting portions. The lower body-supporting portion is pivotally mounted at the end thereof proximate to the upper body-supporting portion for deflection movement about a horizontal axis, side-bending movement about a vertical axis and rotation movement about a longitudinal axis. Locking devices include a clamping element connected to one of two relatively movable portions of the table and a slide element pivotally coupled to the other of the relatively movable portions, the slide element being slidably received in the clamping element. The clamping element may be manually manipulated to clamp the slide element therein to thereby lock the relatively movable table portions at predetermined relative positions.

It is therefore an object of the invention to provide an improved chiropractic table.

It is another object of the invention to provide such a table in which a lower body-supporting portion can be locked in a selected rotation or side-bending position.

Another object of the invention is to provide such a table in which a lower body-supporting portion can be locked in a desired position to obviate the use of a practitioner's hands to stablize or hold the table.

Still another object of the invention is to provide such a table which can be locked in a predetermined, selected position without interferring with other articulation or movement of the table.

Another object of the invention is to provide such a table which can be unlocked to facilitate free rotational and side-bending movement of the lower body-supporting portion.

BRIEF DESCRIPTION OF THE DRAWINGS

The above-mentioned and other features and objects of this invention and the manner of attaining them will become more apparent and the invention itself will be best understood by reference to the following description of an embodiment of the invention taken in conjunction with the accompanying drawings wherein.

DESCRIPTION OF A SPECIFIC EMBODIMENT

Figure 1:
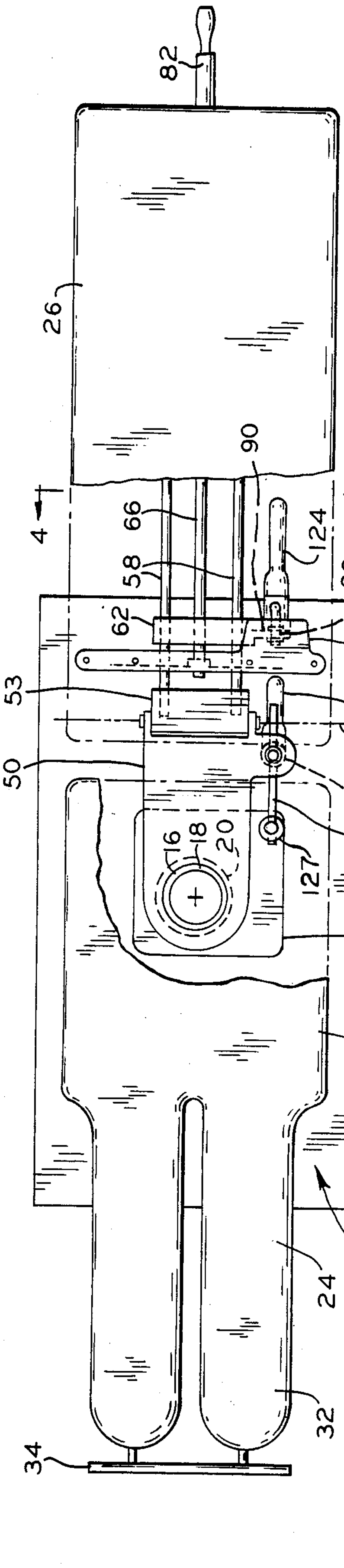
FIG. 1 is a top plan view of a chiropractic treatment table in accordance with the present invention.

Referring now to the drawings, there is illustrated a chiropractic treatment table 10. The table includes a supporting base 12 having a generally flat, rectangular base plate 14 and an upstanding pedestal 16 fixedly secured thereto. Typically, pedestal 16 will include two telescopically engaged members 18, 20 to permit operatively connected vertical adjustment of the table height and rotation therebetween.

A body supporting table 22 is mounted to the pedestal 16. The table 22 is centrally divided into an upper body-supporting portion 24 and a lower body-supporting portion 26. The upper body-supporting portion 24 is provided with a supporting frame 28 which is fixedly secured to pedestal portion 18 and movable therewith. Upper body-supporting portion 24 is further provided with a cushion 30 which is preferably longitudinally bifurcated at its distal end 32 to facilitate a patient lying face down thereon. A slidably adjustable grab bar 34 is slidably coupled to the supporting frame 28, the grab bar 34 being selectively clamped by means of the clamping knobs as at 36. The upper body-supporting portion 24 is locked in a desired elevated or pivoted position by means of a pedestal clamping lever 42 and associated assembly (not shown in the drawings).

Frame 28 includes a hollow collar portion 46 formed as a part of frame member 48, collar 46 being spaced from pedestal 16 toward lower body-supporting portion 26.

The lower body-supporting portion 26 includes a pivot plate structure 50 by means of which lower body-supporting portion 26 is pivotable relative to the upper body-supporting portion 22 about a vertical axis 52. Mounted to the structure 50 is an elongated lower body-supporting portion frame 58. Frame 58 is pivotable about a horizontal deflection axis 60. In the illustrated embodiment, the table is provided with an electrically powered deflection mechanism as described in more detail in copending U.S. Pat. No. 4,489,714 and assigned to the assignee of the present invention. This mechanism controls deflection movement of the lower body portion 26, that is, pivoting movement thereof, about the deflection axis 60.

Figure 3:
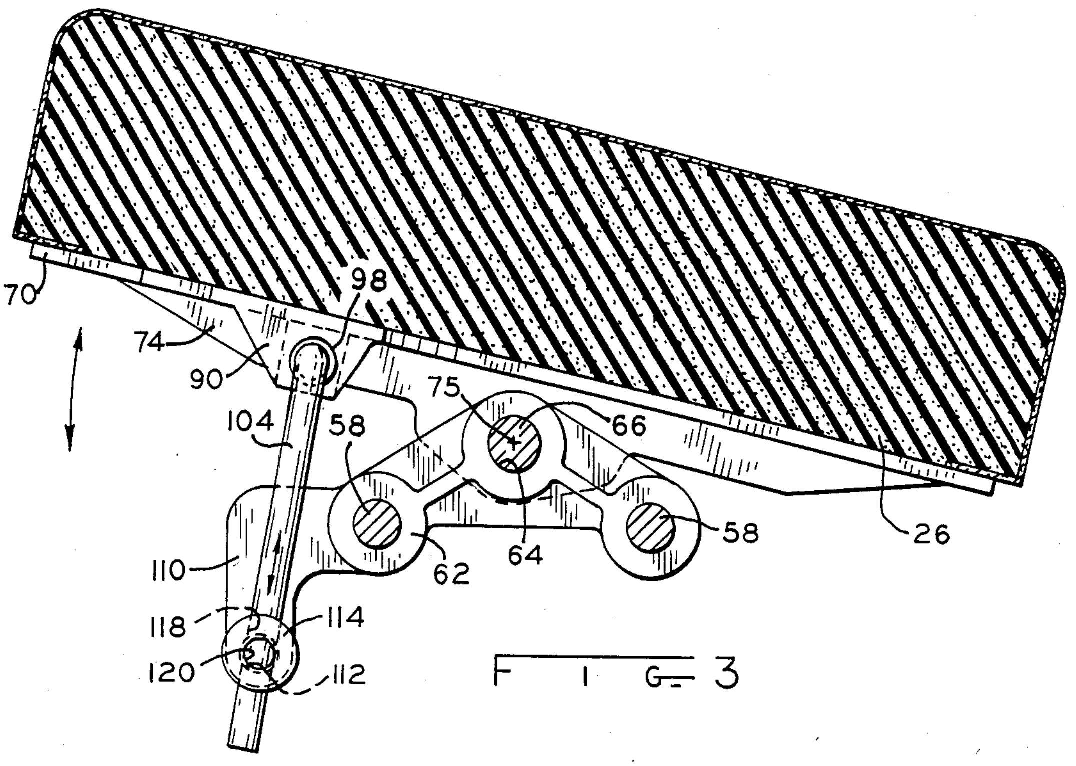
FIG. 3 is a fragmentary longitudinal sectional view taken along section line 3—3 of FIG. 2.

Frame 58 includes a plurality of laterally extending castings 62. Castings 62 are provided with pivot bearings as at 64 (FIG. 3 only). A rotation shaft 66 is journaled in the bearings 64. The lower body-supporting 26 includes a bed 70 provided with elongated, laterally extending members 72, 74 which are fixedly secured to the shaft 66 for rotation movement about a longitudinally extending, horizontal axis 75.

Figure 2:
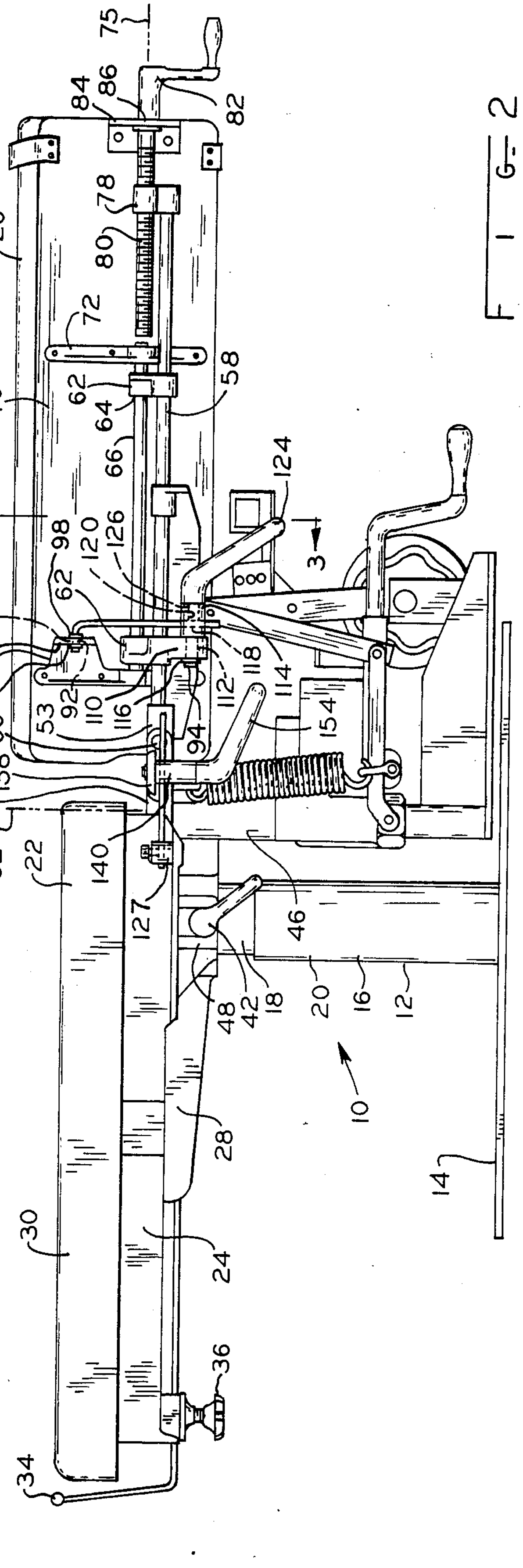
FIG. 2 is a side plan view of the chiropractic treatment table with the lower body-supporting portion thereof shown in its full rotation position.

In FIG. 1, the lower body-supporting portion 26 is shown in its horizontal position and in its full rotation position in FIG. 2. A threaded collar 78, elongated threaded shaft 80, and crank 82 couple frame 58 and to the lower body-supporting portion bed 70 via an angle bracket 84 and interlocking collar 86 to permit longitudinal adjustment of the length of the body-supporting table 22 and in particular the relative position of the lower body-supporting portion 26 relative to the upper body-supporting portion 24.

Thus configured, the chiropractic treatment table 10 is representative of known tables. It will be observed that the table 10 is so constructed that the lower body-supporting portion 26 can be rotated about the side-bending axis 52, referred to as side-bending movement, vertically pivoted about the deflection axis 60, referred to as deflection movement, and pivoted about the rotation axis 75, referred to as rotation movement. These three movements are extensively used by chiropractors in various therapies and procedures. It has now been found desirable, however, to provide a means for locking the lower body portion 26 in predetermined side-bending or rotation positions. Accordingly, and referring particularly to FIGS. 3 and 4, means are provided for locking the lower body-supporting portion in any selected side-bending and/or rotation position.

Figure 5:
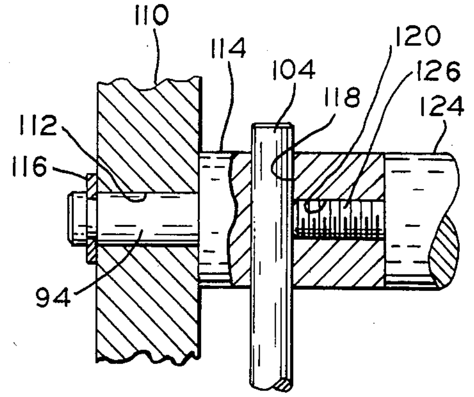
FIG. 5 is a fragmentary sectional view of the rotation movement pivot post.

For rotation locking, and referring particular to FIGS. 3 and 5, the bed member 74 is provided with a downwardly depending flange 90 laterally displaced from rotation axis 75. An elongated locking bar on shaft 104 is provided with a 90° bend. One leg 92 of bar 104 is rotatably received in a journal opening 96 in flange 90 and secured by means of two snap rings 98, 100 (FIG. 5 only). In similar manner, casting 62 is provided with a downwardly depending flange portion 110 having a through hole 112 therethrough. A pivot post 114 has a reduced diameter portion 94 secured in the hole 112 by means of a snap ring or the like 116. A radial through hole 118 extends through the post 114 laterally of its axis and an axial threaded hole 120 communicates therewith from the distal end of the post 114. A manually operable lever (FIGS. 1 and 2 only) is provided with a threaded end portion 126 which is received in the threaded hole 120. The shaft 104 is slidably received in the hole 118. It will now be seen when the clamping lever 124 is rotated to loosen the shaft 104, the lower body-supporting portion 26 can be rotated in normal fashion. When the lower body-supporting portion 26 is in a desired rotation position, it can be clamped in that position by tightening the clamping lever 124.

Figure 4:
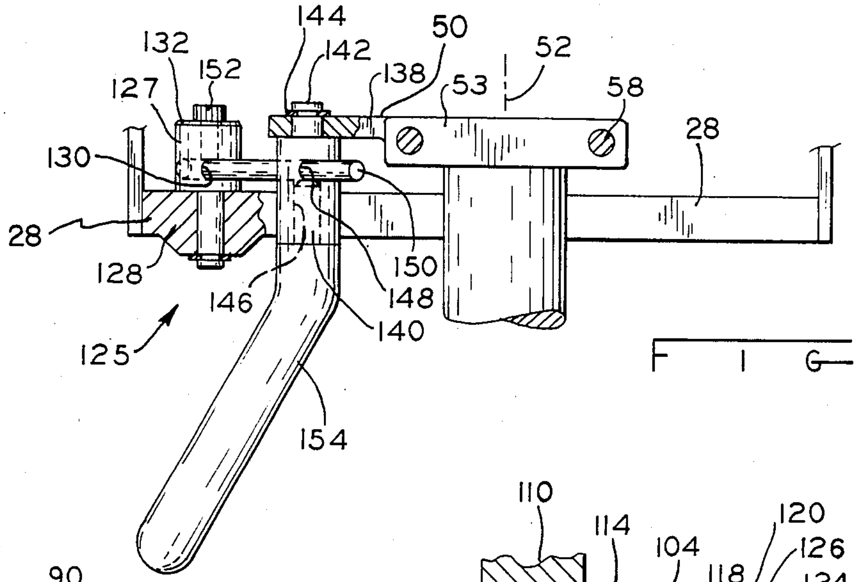
FIG. 4 is a fragmentary sectional view of a portion of the lateral side bending lock taken along section line 4—4 of FIG. 1.
Figure 6:
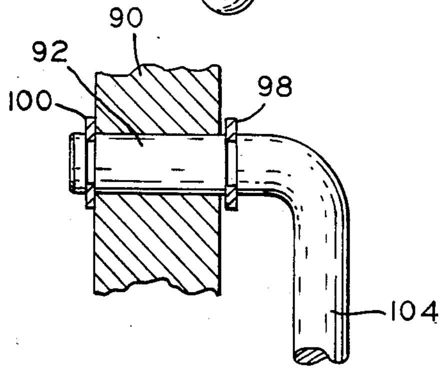
FIG. 6 is a fragmentary sectional view of the rotation movement pivot connection.

Referring now particularly to FIG. 4, the structure of the side-bending lock 125 is shown in detail. This lock mechanism is substantially identical to that used for the rotation lock above described and includes a pivot post 127 which is pivotally connected to a laterally extending boss portion 128 which is formed as a part of the frame 28. Post 127 is provided with a through hole 130 extending therethrough perpendicular to its axis. A threaded hole 132 communicates with the through hole 130 from the distal end of the post 127. The lower body-supporting portion pivot plate structure 50 is also being provided with a laterally extending flange 138 and another pivot post 140 is pivotally coupled thereto by a reduced diameter portion 142 and snap ring fastener as at 144. A threaded hole 146 communicates with a through hole 148 as with the other pivot post. An elongated shaft 150 is fixedly clamped in the post 127 by a threaded fastener 152 and is slidably received in through hole 148. It will now be seen that the lower body-supporting portion 26 can be pivoted about the side-bending axis 52, the shaft 150 is sliding in the hole 148 in response to this movement. When the table is in a desired side-bending position, it can be secured by tightening the clamping lever 154.

From the above description it will now be seen that the chiropractic treatment table 10 of the present invention can be selectively locked in a desired rotation or side-bending position. The locking mechanisms facilitate locking without otherwise interferring with normal movement of the table. The locks can be activated individually or together and can be disengaged to permit normal free movement of the lower body-supporting portion of the table relative to the upper body portion.

While there have been described above the principles of this invention in connection with specific apparatus, it is to be clearly understood that this description is made only by way of example and not as a limitation to the scope of the invention.

What is claimed is:

1. A chiropractic table comprising:

a supporting base, an elongated body supporting table mounted thereon and being centrally divided into upper body-supporting and lower body-supporting portions, said lower body-supporting portion being pivotably mounted at the end thereof proximate to said upper body-supporting portion for deflection movement about a horizontal laterally extending axis, for lateral side-bending movement about a vertical axis, and for rotation movement about the longitudinal axis of said lower body-supporting portion, rotation lock means for locking said lower body-supporting portion in selected rotation position;

side-bending lock means for locking said lower body-supporting portion in a selected side-bending position;

said upper and said lower body-supporting portions each including a supporting frame, adjacent portions of said frames being relatively movable in response to said side-bending movement, said side-bending lock means including an elongated side-bending shaft pivotably connected to one of said relatively movable adjacent portions, said side-bending shaft being slidably received through said side-bending pivot post, and side-bending clamp means for clamping said side-bending shaft to said side-bending pivot post;

said lower body-supporting portion includes a bed portion pivotably mounted to said lower body-supporting portion frame for said rotation movement, said bed and said lower body-supporting frame portion including adjacent portions relatively movable with respect to each other in response to said rotation movement, an elongated rotation shaft pivotably connected at one end thereof to one of said lower body-supporting portion adjacent portions, and a rotation pivot post pivotably connected to the other thereof, said rotation shaft being slidably received through said rotation pivot post, and rotation clamping means for clamping said rotation shaft in a selected position in said rotation pivot post;

said side-bending and said rotation pivot posts are generally cylindrical members having reduced diameter end portions pivotably journaled in said other of said adjacent portions, said pivot posts having a cylindrical hole therethrough extending perpendicular to the axis thereof, said holes having a diameter complementary to the diameter of said rotation and side-bending shafts, and further including a threaded hole extending axially therein and communicating between the distal end of said posts and said cylindrical holes, a threaded element being operatively received in said threaded holes and being axially movable between a position frictionally engaging a respective one of said rotation and side-bending shafts and a second position disengaged therefrom in response to rotation of said threaded element.

2. The table of claim 1 wherein said threaded elements each include a manually operable lever portion on the distal end portion thereof.

* * * * *